United States Patent
Bok et al.

(10) Patent No.: US 7,867,525 B2
(45) Date of Patent: Jan. 11, 2011

(54) POWDER OR EXTRACTS OF PLANT LEAVES WITH ANTI-OBESITY EFFECTS AND ANTI-OBESITY FOOD COMPRISING THEM

(75) Inventors: Song-Hae Bok, Taejon (KR); Myung-Hee Kim, Taejon (KR); Eun-Eai Kim, Taejon (KR); Mung-Sook Choi, Taegu (KR); Surk-Sik Moon, Konju-si (KR); Kyu-Tae Chang, Taejon (KR)

(73) Assignee: Bionutrigen Co., Ltd., Taejon (KR)

( * ) Notice: Subject to any disclaimer, the term of this patent is extended or adjusted under 35 U.S.C. 154(b) by 1119 days.

(21) Appl. No.: 10/640,650

(22) Filed: Aug. 14, 2003

(65) Prior Publication Data

US 2005/0003026 A1    Jan. 6, 2005

(30) Foreign Application Priority Data

| Aug. 14, 2002 | (KR) | ............ 10-2002-0048037 |
| Oct. 23, 2002 | (KR) | ............ 10-2002-0064919 |
| Oct. 23, 2002 | (KR) | ............ 10-2002-0064920 |
| Nov. 8, 2002 | (KR) | ............ 10-2002-0069234 |
| Nov. 8, 2002 | (KR) | ............ 10-2002-0069235 |
| Apr. 29, 2003 | (KR) | ............ 10-2003-0026979 |
| Apr. 29, 2003 | (KR) | ............ 10-2003-0026980 |
| Apr. 29, 2003 | (KR) | ............ 10-2003-0026981 |
| Apr. 29, 2003 | (KR) | ............ 10-2003-0026982 |
| Apr. 29, 2003 | (KR) | ............ 10-2003-0026983 |
| Apr. 29, 2003 | (KR) | ............ 10-2003-0026984 |
| May 6, 2003 | (KR) | ............ 10-2003-0028529 |
| May 6, 2003 | (KR) | ............ 10-2003-0028530 |

(51) Int. Cl.
*A61K 36/254* (2006.01)
*A61K 36/00* (2006.01)

(52) U.S. Cl. .............. 424/728; 424/725; 424/774; 424/778

(58) Field of Classification Search .............. None
See application file for complete search history.

(56) References Cited

U.S. PATENT DOCUMENTS

| 4,042,688 A | 8/1977 | Gans et al. |
| 4,497,800 A | 2/1985 | Larson et al. |
| 4,959,350 A | 9/1990 | Frokjaer et al. |
| 5,763,414 A | 6/1998 | Bok et al. |
| 5,792,461 A | 8/1998 | Bok et al. |
| 5,877,208 A | 3/1999 | Bok et al. |
| 5,976,580 A | 11/1999 | Ivey et al. |
| 6,133,311 A | 10/2000 | Bok et al. |
| 6,165,984 A | 12/2000 | Bok et al. |
| 6,221,357 B1 | 4/2001 | Bok et al. |
| 6,277,393 B1 * | 8/2001 | Yrjanheikki et al. ........ 424/426 |
| 6,277,396 B1 * | 8/2001 | Dente .......................... 424/439 |
| 6,313,171 B1 | 11/2001 | Bok et al. |
| 6,509,372 B2 | 1/2003 | Bok et al. |

FOREIGN PATENT DOCUMENTS

| JP | 09149780 A | * | 6/1997 |
| JP | 09227398 A | * | 9/1997 |
| JP | 10000071 A | * | 1/1998 |
| JP | 11310531 A | * | 11/1999 |
| JP | 2000319190 A | * | 11/2000 |
| KR | 1995-0023321 A | | 8/1995 |
| KR | 1995-0030864 A | | 12/1995 |
| WO | WO 0041708 A1 | * | 7/2000 |

OTHER PUBLICATIONS

'Vegetables and Fruits for Health the Pyramid Wat Fact Sheet Seies'. Bulletin #4308. Internet Archive Date: May 1, 1999. [retrieved on Jun. 20, 2007]. Retrived from the Internet: <URL: (http://web.archive.org/web/*/http://www.umext.maine.edu/onlinepubs/htmpubs/4308.htm>.*

Byoung-Mog Kwon et al., *Planta Medica*, vol. 63, (Dec. 6, 1997), pp. 552-553.

"Obesity Drug Pipeline Not So Fat", *Science*, vol. 299, (Feb. 7, 2003), pp. 849-850.

Myung-Sook Choi et al., *Annals of Nutrition & Metabolism 2001*, vol. 45, (Feb. 20, 2001), pp. 195-201.

Sung-Heui Lee M.S., *Nutrition Research*, vol. 19, No. 8, (1999), pp. 1245-1258.

Song-Hae Bok et al., *Int. J. Vitam. Nutr. Res.*, vol. 72, No. 3, (2002), pp. 161-169.

Jeong-Sun Lee et al., *Clinica Chimica Acta*, vol. 314, (2001), pp. 221-229.

* cited by examiner

*Primary Examiner*—Amy L Clark
(74) *Attorney, Agent, or Firm*—Birch, Stewart, Kolasch & Birch, LLP

(57) ABSTRACT

Disclosed are powders or extracts of plant leaves with anti-obesity effects and anti-obesity foods comprising them, and more particularly, anti-obesity food compositions comprising powders or extracts of one or more selected from group consisting of persimmon (*Diospyros KakI* Thunb.) leaves, buckwheat (*Fagopyrum esculentum*) leaves, Chinese matrimony vine (*Lycium chinense*) leaves, endive (*Cichorium endivia*) leaves, and ginseng (*Panax ginseng*). Also disclosed are compositions comprising plant extracts or powders to reduce the weight of animals or humans, and more particularly, boiling water extracts of persimmon leaves, buckwheat leaves and Chinese matrimony vine leaves and persimmon leaf powder, buckwheat leaf powder and Chinese matrimony vine leaf powder were prepared and administered to animals or humans to confirm the effects of reduction of their weight and then health foods comprising the extracts or powders are produced.

23 Claims, No Drawings

POWDER OR EXTRACTS OF PLANT LEAVES WITH ANTI-OBESITY EFFECTS AND ANTI-OBESITY FOOD COMPRISING THEM

This nonprovisional application claims priority under 35 U.S.C. §119(a) on Patent Application Nos. 2002-48037, 2002-64919, 2002-64920, 2002-69234, 2002-69235, 2003-26979, 2003-26980, 2003-26981, 2003-26982, 2003-26983, 2003-26984, 2003-28529, and 2003-28530 filed in Korea on Aug. 14, 2002, Oct. 23, 2002, Oct. 23, 2002, Nov. 8, 2002, Nov. 8, 2002, Apr. 29, 2003, Apr. 29, 2003, Apr. 29, 2003, Apr. 29, 2003, Apr. 29, 2003, Apr. 29, 2003, May 6, 2003, and May 6, 2003, respectively, which are herein incorporated by reference.

THE FIELD OF THE INVENTION

The present invention relates to powder or extracts of plant leaves with anti-obesity effects and anti-obesity food comprising them. More particularly, the present invention relates to anti-obesity food compositions comprising powder or extracts of one or more ingredient selected from the group consisting of persimmon leaves, buckwheat leaves, Chinese matrimony vine leaves, endive leaves, and ginseng.

DESCRIPTION OF THE RELATED ART

As people get well-nourished with improvement of dietary life, the average life expectancy is extended. However, the number of obese people is increasing dramatically every year owing to the westernized dietary life, the excessive intake of food, and the want of physical exercise.

Obesity is a risk factor for major diseases of adult people, related to the generation and acceleration of progress of the diseases of adult people. These diseases include examples such as hypertension, diabetics, arteriosclerosis, stroke, heart failure, and tumors of various kinds, etc. Obese people have a risk of contracting these diseases of adult people at a rate three to six times higher than that of normal people. Therefore, obesity is not only a problem of external appearance, but also an important problem related directly to health.

To prevent obesity, it is important to maintain the present amount of diet and increase the amount of exercise. In the case of being obese, it is desirable to maintain normal weight through appropriate diet after understanding the reason that bodies can metabolize food normally.

As obesity becomes a problem of modern society, the word 'diet' is gathering interest of many people living in modern society. Obese people are very interested in and exert themselves in relation to a reduction of their weight. Consequently, many methods for reducing one's weight, such as fasting, using vegetable enzymes, diarrhea remedies and diuretics, liposuction, single food diets, such as apple diets, grape diets and emperor diets, intake of dietary fiber, moxibustion, original infrared sauna, toning system etc., have been introduced up to now.

These methods, however, place a special stress on the effects of reducing weight and lack an understanding of the accurate and scientific principles of diet, the process of the human body's metabolism, and a nutritious physiological approach. Therefore, these methods lead to a disproportion in nourishment and abnormal body metabolism.

On the other hand, as methods for reducing weight, there are medicinal therapies using inhibitors of appetite, such as amphetamine derivatives etc. However, such medicinal therapies do not maintain inhibition of appetite and have side effects, such as headache, insomnia, elevation of blood pressure, anxiousness, tenseness, hallucinations, vertigo, failing of eyesight, etc. as temporary effects.

Now, as remedies for obesity, there are sold REDUCTIL® for reducing the amount of food ingested by reducing appetite and XENICAL®, an inhibitor of lipases that include enzymes for resolving lipid. It is known that REDUCTIL® acts on the nervous system to reduce appetite in a manner similar to substances of the amphetamine line. However, it is reported that it has side effects, such as elevating blood pressure, etc. It is also known that XENICAL® inhibits the reaction of the enzyme lipase in the intestine so that the absorption and resolution of lipids is hindered. Moreover, it is reported that XENICAL® has effects on the reduction of body fat as weak as only 2% of body weight and it is accompanied by serious abdominal pain and diarrhea. (*Science* 299:849-850, 2003). Accordingly, there is a demand for the development of safe and effective agents for the prevention and remedy of obesity.

In addition, the method of reducing and adjusting body weight using diuretics, has side effects such as kidney toxicity, heart failure, vomiting, etc.

In addition, although central nervous system appetite inhibitors have excellent effects on reduction of weight, people develop a tolerance to them after a certain period of use so that the effects are dramatically decreased. Use of such appetite inhibits is also often accompanied by side effects such as headache, insomnia, dizziness, etc.

Therefore, it is necessary to develop not remedies synthesized artificially, but rather diet compositions provided in the form of food from herbal medicines we have consumed up to now.

Let's look at various conventional documents related to diet foods, for example, U.S. Pat. No. 4,959,350 discloses diet compositions which comprise a balanced diet of an aqueous medium mixture of fat, carbohydrate, and dietary nitrogen compounds. Korean official report for publication of patent No. 95-23321 discloses a diet food substituted for meals manufactured by adding essential nutrients such as minerals, vitamins, proteins, etc., to powder containing Psyllium Husk.

In addition, Korean official report for publication of patent No. 95-30864 discloses a low calorie diet food comprising abundant dietary fiber, which is manufactured by combining corn grits, apple peels, residue in the preparation of bean curd, wheat bran, hulls of corn, hulls of rice, α-cellulose, β-cyclodextrin, pectin, aspartame, etc. and extruding the combined ingredients at high temperature. U.S. Pat. No. 4,497,800 teaches diet compositions in stable emulsion form comprising proteins including free amino acids and a small amount of peptides, carbohydrates including maltodextrin, the minimum quantity of minerals and vitamins and stabilizers, etc. U.S. Pat. No. 4,042,688 teaches a method of providing high-protein nutrient by oral administration of a predigested protein composition containing essential amino acids. Further, U.S. Pat. No. 5,976,580 discloses a nutrient composition containing additives obtained from microbes, viruses, pectin, and polysaccharides, or nucleic acids.

Conventional diet foods have placed an emphasis on methods for resolving fat accumulated in bodies for remedy of obesity. However, there have been few studies performed on the development of diet foods using normal foods.

A research team of Bionutrigen Co., Ltd. and Korea Research Institute of Bioscience and Biotechnology has confirmed that vegetable extracts have great effects on lipid metabolism in humans and animals through papers and patents exemplified below for the last 10 years.

For example, it has been known that the polyacetylen analogue panaxyal included in ginseng inhibits the activity of the enzyme, acyl coA:cholesterol acyltransferase (ACAT) which is involved in absorption of cholesterol in the intestine (*Planta Med.* 63: 552-553, 1997). Accordingly, administration of ginseng results in reduction of the amount of cholesterol absorbed into bodies from consumed food.

It was confirmed that bioflavonoids, such as hesperidin, hesperetin, etc., included in fruit peels and leaves of oranges, lemons, tangerines, and citrons, etc., reduce the amount of cholesterol and triglycerides in the blood and liver of animals. Also resulting was a reduction in the activity of 3-hydroxy-3-methyl glutaryl coA (HMGA) reductase, which is involved in the synthesis of cholesterol and ACAT, which is involved in absorption of cholesterol into bodies in the intestine. Also resulting was prevention of arteriosclerosis, etc., by reducing the amount of cholesterol in the blood and the speed of lipid synthesis in humans or animals, and aiding in blood circulation by preventing blood cells from aggregating together (*Nutrition Res,* 19: 1245-1258, 1999, *Int. J. For vitamin & nutrition Research* 71: 36-44, 2001, *J. Nutrition.* 129: 1182-1185), 1999, U.S. Pat. No. 6,221,357, 2001. Apr. 4, U.S. Pat. No. 5,792,461, 1999. Aug., 11, U.S. Pat. No. 5,763,414, 1998. Jun. 9).

It was also confirmed that bioflavonoids, such as narinsin, narinsenin, etc., abundant in jamong-peel also reduce serum cholesterol, serum triglycerides and triglycerides in the liver, and reduce the activity of HMGA reductase and the enzyme ACAT (*Ann. Nutr. Metab.* 45: 193-201, 2001, U.S. Pat. No. 5,877,208, 1999. Mar. 2, U.S. Pat. No. 6,165,984, 2000. Dec. 26).

The polyphenol line of substances, such as Rutin, and Quercetin, included in many plants such as buckwheat leaves, flowers and onions, etc., also reduce the amount of cholesterol and lipids in the blood and the liver, and reduce the activity of HMGA reductase and the enzyme ACAT (*Nutrition Research* 22: 283-295, 2002, *Int. J. Vitamin Nutr. Res* 72: 161-169, 2002, U.S. Pat. No. 6,509,372 2003. Jan. 21).

It is confirmed that 4-hydroxycinnamate, 3,4-dihydroxycinnamate, 3,4-dihydroxyhydrocinnamate, etc., included in many plants, reduce the amount of cholesterol and triglycerides in the blood and liver of animals (*Ann. Nutr. Metab.* 47: 144-151, 2003, *Clinica Chimica Acta* 314: 221-229, 2001, U.S. Pat. No. 6,313,171, 2001. Nov. 6).

It was also confirmed that the polyphenol line substances, such as tannin, included in various plants, as well as catechin, etc., included in green tea, are effective on improving lipid metabolism of animals and humans and generally inhibit the activity of enzymes engaged in the synthesis of lipids, such as cholesterol, triglycerides, etc., (U.S. Pat. No. 6,133,311 2000, Oct. 17).

It has also been known that persimmon leaves are effective on chronic diseases such as hypertension, arteriosclerosis, heart disease, and diabetes. Persimmon leaves comprise flavonoids, such as astragalin, myrincitrin, organic acids, such as tannin, polyphenols, betulic acid, oleanic acid and ursolic acid, and chlorophyll and vitamins, such as vitamin C and inorganic salts in abundance. Persimmon leaves thus have a probability of improving lipid metabolism.

The present research team has investigated the development of raw materials of foods, beverages, and medicines for prevention of cardiovascular diseases (especially high serum lipids and arteriosclerosis) by using the extracts of plants which we can take in safely and harmlessly.

During progressing this study, we have investigated the probability of increasing anti-obesity effects due to the combined effects of various plant extracts, for example, tannins, bioflavonoids, and the polyphenol line substances and dietary fibers, for example, cellulose, pectin, mannan and gallactan etc. when the ingredients are consumed together in the form of ground plant leaves, branches and roots including them.

Also, during progress in this study, we discovered that boiling water extracts of some vegetables inhibited increase of the weight of mice so that we started to develop anti-obesity medicines (Korean patent application 02/48037, 02/63953, 02/64919, 02/64920, 02/69234, 02/69235, 03/26983, 03/26981, 03/26983, 03/26980, 03/26984, 03, 26979, 03/28529, 03/28530).

The development of food materials which we usually eat as diet foods, has advantages in that it is not necessary to use assistant medicines for diet, there is no burden of taking medicine and fasting to reduce weight, by which obese people may be satisfied psychologically.

Persimmon trees grow wild all over many countries and contain glycoside flavonoids, tannins, substances of the phenol line, resins, cacumin line compounds, reducing sugars, polysaccharides, refined oils, organic acids, chlorophyll, etc., and the glycoside flavonoids contains astragarin, mirystrin, and especially abundant vitamin C in amounts of about 100 mg per 100 g in persimmon leaves sampled from April to June.

Persimmon leaves are known to be good for protecting bronchus through folk remedies and for helping absorption of minerals, such as chalybeate, which are easily lost after excessive drinking owing to their abundant vitamin C.

And yet, there has been no attempt to reduce weight using persimmon leaves.

In addition, it is reported that buckwheat has anti-oxidative effects on the body and effects in reducing blood pressure etc, to be used for treatment of vascular diseases. It has a bright yellow or normal yellow color. Rutin, a kind of flavonoid, acts on energy conversion reactions in mitochondria and chloroplasts and has effects on inhibiting lipid peroxidation in mitochondria. It is also known that buckwheat is effective on osteoporosis, adjusting blood pressure, and anemia owing to its abundant nutrients, such as calcium, iron, protein, various kinds of essential amino acids, and niacin, etc.

However, there has been no attempt to reduce weight using buckwheat leaves.

Chinese matrimony vines are oval or long elliptical in shape and the 1.5-2.5 cm long plant matures and is harvested from July to the latter part of November. There are different kinds, such as the original species, Cheong Yang species, Japanese No. 1 that came from Japan, and Chinese No. 1, the first that came from China. They contain proteins, lipids, glucides, calcium, phosphorus, iron, betain, rutin, and vitamins (A, B1, B2, C), etc., which are absorbed quickly. In Chinese medicine, they are used for tonic medicines or refrigerant medicines and have been known to have excellent protective effects on the function of liver and few side effects. It is also known that they recover one's sight, prevent diseases of adult people, such as diabetics, improve the function of lung and kidney, prevent white hair from rising by spreading on hair after mixing with *perilla* oil and maturing, and are effective on burns.

However, there has been no attempt to reduce weight using Chinese matrimony vine leaves.

The present inventors have made every effort to develop compositions for preventing obesity using persimmon leaves, buckwheat leaves, Chinese matrimony vine leaves, endive leaves, and ginseng powder. The inventors have confirmed that persimmon leaves, buckwheat leaves, Chinese matrimony vine leaves, endive leaves, and ginseng powder are effective on reducing weight. The inventors have made every effort to develop anti-obesity dietary fibers, anti-obesity beverages, anti-obesity uncooked food compositions, anti-obesity powder, anti-obesity fast-food for cooking hamburger, anti-obesity sausages, anti-obesity carbohydrates food, anti-obesity coffee, anti-obesity green tea and herb tea, anti-obesity artificial flavors, anti-obesity vegetable juices and source, anti-obesity salad, anti-obesity Kim Chi, etc.

DISCLOSURE OF INVENTION

It is an object of the present invention to provide methods for manufacturing dietary fibers from persimmon leaves, buckwheat leaves, Chinese matrimony vine leaves, endive leaves, and ginseng, which are effective on inhibiting obesity.

DETAILED DESCRIPTION OF THE PREFERRED EMBODIMENT

The present invention is explained in detail by the following examples. However, the examples are provided for illustration of the present invention, not for limitation thereof.

The following percentages about solid among solid, liquid among liquid, solid among liquid are weight/weight, volume/volume, weight/volume, respectively and all reactions were performed at room temperature unless stated otherwise.

Example 1

Preparation of Extracts of Plant Leaves 2.6 kg of dried persimmon leaves was prepared by being washed thoroughly and dried in the shade at normal temperatures for 1 week. To the dried leaves, 18.0 L of water was added, boiled at 100° for 1.5 hours and filtered to obtain an extract and a solid remnant. The solid remnant was extracted one more time by the above-mentioned method. The obtained extracts were combined, condensed under reduced pressure and lyophilized to obtain 0.5 kg of extracted persimmon leaf powder.

3.0 kg of dried buckwheat leaves was prepared by being washed thoroughly and dried in the shade at normal temperatures for 1 week. To the dried leaves, 20.0 L of water was added, boiled at 100° for 1.5 hours and filtered to obtain an extract and a solid remnant. The solid remnant was extracted one more time by the above-mentioned method. The obtained extracts were combined, condensed under reduced pressure and lyophilized to obtain 0.6 kg of extracted buckwheat leaf powder.

2.9 kg of dried Chinese matrimony vine leaves was prepared by being washed thoroughly and dried in the shade at normal temperatures for 1 week. To the dried leaves, 20.0 L of water was added, boiled in 100° for 1.5 hours and filtered to obtain an extract and a solid remnant. The solid remnant was extracted one more time by the above-mentioned method. The obtained extracts were combined, condensed under reduced pressure and lyophilized to obtain 0.6 kg of extracted Chinese matrimony vine leaf powder.

An extract of endive leaf powder was also prepared by the above-mentioned method.

Example 2

Anti-Obesity Effects of Persimmon Leaves, Buckwheat Leaves, and the Extracts Thereof in Animals 1. Raising Experimental Animals 40 4 week old, male Sprague-Dawley (Bio genomics co. Ltd.) rats that weigh 90-110 g were divided into four groups by a randomized block design. The four groups of rats were fed different diets respectively as shown the following Table 1. More particularly the groups were fed the following: AIN-76 diet composition for experimental animals containing 1% cholesterol (Teklad, Madison, U.S.)(control); AIN-76 diet composition for experimental animals containing 1% cholesterol and 0.2% of boiling water extract of persimmon leaves; AIN-76 diet composition for experimental animals containing 1% cholesterol and 0.077% of boiling water extract of buckwheat leaves; AIN-76 diet composition for experimental animals containing 1% cholesterol and 0.277% boiling water extracts of a mixture of persimmon leaves and buckwheat leaves (0.2% boiling water extract of persimmon leaves and 0.077% boiling water extract of buckwheat leaves).

TABLE 1

The components of experimental animal's diet compositions

| Components | Control | Boiling water extract of persimmon leaves | Boiling water extract of buckwheat leaves | Boiling water extracts of a mixture of persimmon leaves and buckwheat leaves |
|---|---|---|---|---|
| Casein | 20 | 20 | 20 | 20 |
| D,L-methionine | 0.3 | 0.3 | 0.3 | 0.3 |
| Corn starch | 15 | 15 | 15 | 15 |
| Sucrose | 49 | 48.800 | 48.923 | 48.723 |
| Cellulose Powder | 5 | 5 | 5 | 5 |
| Mineral mixture *1 | 3.5 | 3.5 | 3.5 | 3.5 |
| Vitamin mixture *2 | 1 | 1 | 1 | 1 |
| Choline bitatrate | 0.2 | 0.2 | 0.2 | 0.2 |
| Corn oil | 5 | 5 | 5 | 5 |
| Cholesterol | 1 | 1 | 1 | 1 |
| Boiling water extract of persimmon leaves | — | 0.2 | — | — |
| Boiling water extract of buckwheat leaves | — | — | 0.077 | — |

TABLE 1-continued

The components of experimental animal's diet compositions

| Components | Control | Boiling water extract of persimmon leaves | Boiling water extract of buckwheat leaves | Boiling water extracts of a mixture of persimmon leaves and buckwheat leaves |
|---|---|---|---|---|
| Boiling water extracts of a mixture of persimmon leaves and buckwheat leaves *3 | — | — | — | 0.277 |
| Total | 100 | 100 | 100 | 100 |

*1 AIN-76 mineral mixture (TEKLAD premier Co., Madison, WI, U.S.A.)
*2 AIN-76 vitamin mixture (TEKLAD premier Co., Madison, WI, U.S.A.)
*3 Boiling water extracts of mixture of persimmon leaves and buckwheat leaves: 1% cholesterol + 0.2% of the boiling water extract of persimmon leaves + 0.077% of the boiling water extract of buckwheat leaves Experimental diets were stored cold and were fed in ad libitum. The intake amount was measured and recorded every day and the weight of the rats was measured every five days. All rats showed a normal rate of growth.

2. Measurement of the Body Weight Increased, the Intake Amount and the Weight of Organ The intake effects of boiling water extract of persimmon leaves, buckwheat leaves, a mixture of persimmon leaves and buckwheat leaves on rats' body weight and organ weight was as follows.

The weight increase and the intake amount of the four groups of rats raised by the above method were measured every five days and reported with mean±standard deviation in Table 2.

After a breeding time of five weeks ended, the rats were and anesthetized, and each organ was extracted and was washed with a saline solution. After removal of water on the surface of the organs by gauze, the weight was measured and the mean±standard deviation is shown in Table 2.

TABLE 2

The amount of change of rats' weight

| Groups | Increase of weight (g/day) | The amount of diet consumed (g/day) | Weight of organ (g) | | |
|---|---|---|---|---|---|
| | | | Liver | Heart | Kidney |
| Control | 7.87 ± 0.20 | 24.54 ± 0.21 | 16.54 ± 0.58 | 1.49 ± 0.03 | 3.15 ± 0.08 |
| Boiling water extract of persimmon leaves | 7.20 ± 0.21 | 24.50 ± 0.24 | 15.87 ± 0.65 | 1.36 ± 0.04 | 3.09 ± 0.11 |
| Boiling water extract of buckwheat leaves | 7.60 ± 0.11 | 24.23 ± 0.21 | 16.85 ± 0.35 | 1.35 ± 0.02 | 3.10 ± 0.04 |
| Boiling water extracts of a mixture of persimmon leaves and buckwheat leaves | 7.10 ± 0.21 | 24.59 ± 0.35 | 16.44 ± 0.43 | 1.37 ± 0.05 | 2.91 ± 0.09 |

As seen in the above Table 2, in comparison with the control group, the rate of increase of weight decreased 8.50%, 3.5% and 10.0% by administering boiling water extract of persimmon leaves, boiling water extract of buckwheat leaves, and boiling water extracts of a mixture of persimmon leaves and buckwheat leaves, respectively. Through the above-mentioned result, the inventors knew that in comparison with the control group, the present invention, boiling water extract of persimmon leaves, boiling water extract of buckwheat leaves, and boiling water extracts of a mixture of persimmon leaves and buckwheat leaves had the effect of significantly decreasing or inhibiting increase in weight. Therefore, then inventors predicted that boiling water extract of persimmon leaves, boiling water extract of buckwheat leaves, boiling water extracts of a mixture of persimmon leaves and buckwheat leaves are very useful in reducing weight.

Example 3

Manufacturing Plant Powder

After collecting persimmon leaves from the beginning of July to the beginning of August and drying them at room temperature, the inventors ground them by grinder to 100 mesh size.

At the point in time when the flower put forth the first bud while the buckwheat grew (the height was about 30-40 cm), the inventors collected buckwheat leaves, dried them at room temperature, and then reduced them to powder.

At the point in time when new buds of Chinese matrimony vines sprouted and they grew to be 20-30 cm high, the inventors collected Chinese matrimony vine leaves, dried them at room temperature, and then reduced them to powder. During cultivation, the inventors did not use agricultural chemicals and mainly used many organic fertilizers.

Endive leaves were obtained, dried at room temperature, and then reduced to powder according to above-mentioned method.

Example 4

The Anti-Obesity Effects of Plant Powder

The plant powders were consumed by humans in an amount of 5-20 g for 10-30 days. Then, analysis of body fat, weight, liver function (GOT, GPT, r-GTP), serum cholesterol, serum triglycerides, LDL and HDL, etc. were performed to confirm their effects on human bodies. During the experimental term, the subjects abstained from exercise and maintained a normal diet.

The dried powder of persimmon leaves was consumed in an amount of 10 g per day for thirty days and blood was extracted and analyzed. In comparison with levels before the intake, body weight decreased 1.5 kg (−1.8%), body fat decreased 2.8 kg (−12%), serum cholesterol decreased 12%, HDL increased 19%, GOT decreased 29%, (66→53), GPT decreased 43%, (109→62), rGTP decreased 10%, (70→63). It is therefore, concluded that the intake of the powder of persimmon leaves can cause useful effects on human health such as reducing weight, reducing body fat, reduction of production of serum lipids, and improvement of liver function.

The dried powder of buckwheat leaves was consumed by humans in an amount of 10 g per day for fifteen days. Then, blood was extracted and analyzed and the inventors obtained the following results: weight decreased 0.7 kg (−1.3%), and body fat decreased 0.7 kg (−4%).

The powder of Chinese matrimony vine leaves was consumed in an amount of 20 g per day for 22 days. Weight decreased 0.2 kg, and body fat decreased 1.4 kg (−6.7%).

The powder of persimmon leaves 5 g, the powder of buckwheat leaves 5 g, and the powder of endive leaves 10 g were consumed every day. After 21 days, blood was extracted and analyzed. Weight decreased 1.80 kg (−2.3%), body fat decreased 0.5 kg (−2.3%), serum cholesterol decreased 11%, LDL decreased 10%, serum triglycerides decreased 5%, GOT decreased 7%, GPT decreased 20%, and rGPT decreased 27%. Generally, body fat was reduced, the amount of production of serum lipids was reduced, and liver function was improved.

Example 5

Anti-Obesity Effects of Administering Powder of Ginseng and Plants Comprising Polyphenols and Bioflavonoids into Human Body Anti-obesity compositions comprising plant powder that were confirmed to improve liver function in the above example were prepared as in the following Table 3. After the compositions of Table 3 were consumed by 10 people in amounts of 5 g per day for 2 weeks, a blood test was performed. The blood test showed that the amount of total cholesterol decreased by an average of 5%.

TABLE 3

The composition ratio of the composition comprising powder or extract of ginseng and plant containing polyphenols and bioflavonoids

| Ingredients | Ratio(Weight %) |
|---|---|
| powder of ginseng | 12.5 |
| powder of garlic | 17.5 |
| powder of jujube | 12.5 |
| powder of onion | 7.5 |
| powder of persimmon leaves | 11.5 |
| powder of orange-peels | 5.5 |
| powder of Chinese matrimony vine leaves | 16.5 |
| powder of buckwheat leaves | 16.5 |
| Total | 100 |

Example 6

Anti-Obesity Effects of Administering Powder of Ginseng and Plants Comprising Polyphenols and Bioflavonoids into Animals To investigate the in vivo activity related to obesity of the composition provided by Table 3, 3 week old rats were quarantined for acclimatization for 1 week by ordered feed for experimental animals in a breeding-farm for experimental animals bred by an ad libitum method. Rats confirmed healthy were used. 4 week old rats were thus used for the experiment. The environmental provisions of barrier system for the breeding-farm was as follows: temperature: 23±1°, humidity: 55±5%, the frequency of ventilation: 15 times per one hour, illumination time: light 12 hours/dark 12 hours, intensity of illumination: 150-300 lux, ammonia odor: below 200 ppm, noise: below 60 db, air current: below 0.1 m/sec, and was applied to the breeding environment. Four rats per a cage were accommodated and raised using wire cages [for rat, 410*220*200 mm]. Water which was sterilized by high pressure steam at 121° for twenty minutes was used for providing water and sterilized ordered feed [Oriental Co., Ltd. Japan] comprising 2% cholesterol was additionally used for experimental animals by ad libitum.

To examine the effects on inhibiting obesity of the composition represented in Table 3, the compositions were administered to experimental animals as a feed component 5% and the examination was conducted for thirty days.

In comparison to a 3.4% increase of weight in the control group, the weight of the animal groups administered the active composition (Table 3) increased only 2% and there appeared no external symptoms of virulence (Table 4). The experimental results confirmed in Table 4 that the compositions had anti-obesity effects.

TABLE 4

Effects on reducing weight of the composition comprising powder of ginseng and plants comprising polyphenols and bioflavonoids

| | Control (2% cholesterol) | Experimental groups (2% cholesterol + [Table 3], ginseng composition) |
|---|---|---|
| 0 | 408 | 391 |
| After 1 week | 427 | 383 |
| After 2 week | 416 | 397 |

TABLE 4-continued

Effects on reducing weight of the composition comprising powder of ginseng and plants comprising polyphenols and bioflavonoids

|  | Control (2% cholesterol) | Experimental groups (2% cholesterol + [Table 3], ginseng composition) |
|---|---|---|
| After 3 week | 422 | 406 |
| After 4 week | 422 | 399 |
| Total amount of increase of weight | 14(+3.4%) | 8(+2%) |

Example 7

Anti-Obesity Effects of a Mixture of Ginseng and Orange-Peel

The products containing only ginseng has an effect on inhibiting high blood lipid. But this effect is slight.

40 2 week old, white Sprague-Dawley rats from KOREAN CENTOR OF EXPERIMENTAL ANIMALS in Eumsong Chungbuk, Korea were bred and when they were four weeks, the rats were divided into four groups by a randomized block design. The four groups of rats were fed four different high cholesterol diets: a usual diet (AIN-76 diet for experimental animals) plus cholesterol 1% (control); plus cholesterol 1% and extract of orange-peel 0.2%; plus cholesterol 1% and ginseng (ginseng group) 0.1%; and plus cholesterol 0.1%, extracts of orange-peel 0.2%, and ginseng (ginseng group) 0.1%. Table 5 shows the composition of diets which the four groups consumed.

TABLE 5

The compositions of experimental diets(%)

| Components | Control | The extract of orange-peels | Ginseng | The extracts of orange-peels and ginseng |
|---|---|---|---|---|
| Casein | 20 | 20 | 20 | 20 |
| D,L-methionine | 0.3 | 0.3 | 0.3 | 0.3 |
| Corn starch | 15 | 15 | 15 | 15 |
| Sucrose | 49 | 48.8 | 48.9 | 48.7 |
| Cellulose powder | 5 | 5 | 5 | 5 |
| Mineral mixture | 3.5 | 3.5 | 3.5 | 3.5 |
| Vitamin mixture | 1 | 1 | 1 | 1 |
| Choline citrate | 0.2 | 0.2 | 0.2 | 0.2 |
| Corn oil | 5 | 5 | 5 | 5 |
| Cholesterol | 1 | 1 | 1 | 1 |
| Orange-peels extract | — | 0.2 | — | 0.2 |
| Ginseng powder | — | — | 0.1 | 0.1 |
| Total | 100 | 100 | 100 | 100 |

The rats of all diet groups were fed appropriate diets and water in ad libitum for six weeks, the intake amount was recorded every day and the weight was measured every seven days. After breeding of the animals had finished, the analysis of breeding diary data showed that there was no significant difference in the increase of weight and all rats matured normally.

To investigate the effect of the mixture of orange-peel extract and ginseng on serum cholesterol concentration, blood extracted from the rats of the above four groups was analyzed (Table 6).

TABLE 6

Effect of improving lipid metabolism by administering the mixture of ginseng and extract of orange-peels

|  | Control | Orange-peel extract | Ginseng | Ginseng and Orange-peel extract |
|---|---|---|---|---|
| Total cholesterol (mg/dl) | 148 | 121 | 135 | 111 |
| HDL cholesterol (mg/dl) | 25.7 | 30 | 22.8 | 29.1 |
| HDL/Total cholesterol | 17.5 | 25.6 | 17.1 | 26.3 |

According to Table 6, in comparison with the control group, serum cholesterol decreased 9% and HDL cholesterol decreased 11% in the group administered with ginseng, serum cholesterol decreased 18% and HDL cholesterol increased 17% in the group administered with orange-peel extract, bioflavonoids. The group administered the mixture of ginseng and bioflavonoids together showed total cholesterol decrease of 25% and HDL cholesterol increase of 13%.

In other words, the group administered with the mixture of ginseng and orange-peel extract, bioflavonoids together showed better effect of decreasing total cholesterol by 300% than the one administered ginseng only. Therefore, ginseng products containing a mixture of ginseng and bioflavonoids can improve the effects of improving lipid metabolism in the human body and have better medical effects.

Example 8

Anti-Obesity Effect of Administering Powder of Ginseng and Powder of Chinese Matrimony Vine Leaves to Animals A. Preparing Powder of Chinese Matrimony Vine Leaves.

1.0 kg of Chinese matrimony vine leaves was washed thoroughly and dried in the shade at room temperature for 1 week. 200 g of dried Chinese matrimony vine leaves was obtained. 200 g of powder of Chinese matrimony vine leaves was obtained by grinding the dried Chinese matrimony vine leaves.

B. Preparing a Mixed Powder of Chinese Matrimony Vine Leaves and Ginseng.

Dried Chinese matrimony vine leaves and ginseng were mixed in the ratio of 25:1 respectively and ground to obtain a mixed powder of Chinese matrimony vine leaves and ginseng.

C. Investigating Effects of the Powder of Chinese Matrimony Vine Leaves, the Powder of Ginseng, and Mixed Powder of Chinese Matrimony Vine Leaves and Ginseng on Reducing Weight.

Administrating the powder of Chinese matrimony vine leaves, and the mixed powder of Chinese matrimony vine leaves and ginseng to rats:

Experimental materials;

Experimental materials: the powder of Chinese matrimony vine leaves, the powder of ginseng, and the mixed powder of Chinese matrimony vine leaves and ginseng on reducing weight.

Custody and treatment: Experimental materials were kept in sealed container without light at room temperature. In treating experimental materials and the experimental materials made up, the noteworthy point is based on the information the experimental client supplied.

Animals used for experiment;

Lineage (a source of supply): Sprague Dawley Rat, Male, (Bio genomics Inc. Co., Ltd.)

The number of animals administered (sex), ages, and the range of weight: thirty (male), six weeks old, average weight 180-210 g±15%.

Breeding conditions;

Environmental condition: temperature 23±2°, relative humidity 50±10%, frequency of ventilation: 10~15 times per one hour, illumination time: light 12 hours/dark 12 hours, intensity of illumination: 150-300 lux Breeding box: four rats per cage (during quarantine and acclimatization)/three rats per cage during observation were caged in polycarbonate cage.

Feed and drinks: Pellet feed for breeding rats were fed during acclimatization and high cholesterol diets which comprise 0.5% cholesterol added to powder diets were fed in ad libitum during testing times. The cholesterol was from "Sigma" and drinks were fed with refined filtrated water in ad libitum.

Quarantine and acclimatization: Veterinary medical quarantine of all animals was performed during clinical trials. To select rats which are suitable to practice examination, the animals went through acclimatization for fourteen days to be adapted to the powder feed.

Division of groups: After the acclimatization, groups were divided at random based on weight. In dividing the groups, equality by calculating the average weight and standard deviation was confirmed.

Identification: The breed boxes were labeled with the identification cards noting test number, sex, group number, individual number, dosage, testing times, and the person responsible for the test. Identification was accomplished by indicating individual number on tails with an oil pen.

C. The Construction of Experimental Group: According to Following Table 7, the Composition of Diets was Prepared.

TABLE 7

The construction of experimental groups

| Number | Groups | Number of Rats |
|---|---|---|
| 1 | normal diet (control) | 6 |
| 2 | 0.5% cholesterol + normal diet (control) | 6 |
| 3 | 0.5% cholesterol + normal diet + 0.1% ginseng powder | 6 |
| 4 | 0.5% cholesterol + normal diet + 5% Chinese matrimony vine powder | 6 |
| 5 | 0.5% cholesterol + normal diet + 5% Chinese matrimony vine powder + 0.1% ginseng powder | 6 |

D. Experimental Method

Pelletized 'Purina' feed for rats was pulverized, added cholesterol to 0.5%, stirred sufficiently in a stirrer and distributed in porcelain vessels for eight weeks. Because diet feeds were in not in a pellet form, but rather a powder form, to inhibit the loss of feeds owing to rats' overturning vessels, porcelain vessels which had fit weight were used. (Analysis of feeds. Table 8)

TABLE 8

Diet composition of experimental animals.

| Components | Normal diet (control) | 0.5% of Cholesterol + normal diet | 0.5% of Cholesterol + normal diet + 0.1% of ginseng powder | 0.5% of Cholesterol + normal diet + 5% of Chinese matrimony vine powder | 0.5% of Cholesterol + normal diet + 5% of Chinese matrimony vine powder + 0.1% of ginseng powder |
|---|---|---|---|---|---|
| Animal product | 3.4 | 3.4 | 3.4 | 3.4 | 3.4 |
| Cereal | 91.0 | 91.0 | 91.0 | 91.0 | 91.0 |
| Vitamin | 0.1 | 0.1 | 0.1 | 0.1 | 0.1 |
| Mineral | 0.1 | 0.1 | 0.1 | 0.1 | 0.1 |
| Other | 5.4 | 5.4 | 5.4 | 5.4 | 5.4 |
| Cholesterol | — | 0.5 | 0.5 | 0.5 | 0.5 |
| Ginseng powder | — | — | 0.1 | — | 0.1 |
| Chinese matrimony vine powder | — | — | — | 5 | 5 |

Measuring the Change of Weight During Experimental Period:

The body weight was measured every three days after the experiment began to see the change of weight during the experimental period.

Measuring the Lipid Around Epididymes

Rats were anesthetized by ethyl ether. When examined post mortem, blood was gathered from the abdominal aorta, lipid tissue surrounding epididymis was separated collectively, washed using saline solution, dried of water using filter paper, and then weighed. The lipid tissues around the epididymes were separated collectively if they were separated from the direction of the epididymis because they existed as isolated tissues.

Statistical Management

All experimental values were indicated by mean±standard deviation, Levenes test was practiced. In cases where the dispersions were of same qualities, ANOVA (one-way analysis of variance) was performed. And then, when the inventors observed the matters to be attended to, they judged the matters to be attended to statistically by practicing Dunnett's t-test to find experimental groups that had significant difference.

Experimental Result

After 56 days, the breeding time was over, the rats were anesthetized, and organs were extracted and washed using a saline solution. Then, water was removed from the surface of the organs using gauze, and the organs were weighed (Table 9).

TABLE 9

The weight change of organs and body

| Diet groups | Weight (g) | | Liver (g) | Heart (g) | Kidney (g) | | Lipid around epididymis (g) | |
|---|---|---|---|---|---|---|---|---|
| | 0 hr | After 56 days | | | Left | Right | Left | Right |
| Normal diet | 251 | 498 | 13.9 | 1.5 | 1.6 | 1.6 | 3.5 | 3.7 |
| 0.5% of Cholesterol + normal diet | 252 | 517 | 16.2 | 1.6 | 1.7 | 1.7 | 4.2 | 4.2 |
| 0.5% of Cholesterol + normal diet + 0.1% of ginseng powder | 251 | 478 | 14.7 | 1.5 | 1.6 | 1.6 | 2.8 | 2.8 |
| 0.5% of Cholesterol + normal diet) + 5% of Chinese matrimony vine powder | 250 | 475 | 13.3 | 1.5 | 1.6 | 1.6 | 3.0 | 3.1 |
| 0.5% of Cholesterol + normal diet + 5% of Chinese matrimony vine powder + 0.1% of ginseng powder | 252 | 460 | 13.8 | 1.5 | 1.5 | 1.5 | 2.9 | 3.1 |

As seen in the above-mentioned Table 9, in comparison with the control group, administering the powder of Chinese matrimony vine leaves, and the powder of ginseng cause a decrease in body weight of 8%, and 7.5% respectively. And, administering the mixed powder of Chinese matrimony vine leaves and ginseng had better effects on reducing weight with a decrease in body weight of 11%.

Also, the groups administered the powder of Chinese matrimony vine leaves, or the powder of ginseng had decreased lipid layers around epididymes of 34% and 29%, respectively.

Example 9
Anti-Obesity Diet Fiber Composition

An object of the present invention is to provide anti-obesity foodstuffs using persimmon leaves, buckwheat leaves, Chinese matrimony vine leaves, and endive leaves which are confirmed effective on inhibiting obesity in the above-mentioned examples.

The present invention provides an anti-obesity composition comprising one or more ingredient selected from the group consisting of dried and pulverized persimmon leaves, buckwheat leaves, Chinese matrimony vine leaves, endive leaves, and ginseng.

Preferably, the anti-obesity composition further comprises one or more ingredient selected from the group consisting of dried and pulverized red pepper leaves, ripe cowpea leaves, bean leaves, barley leaves, wheat leaves, oat leaves, orange-peel, citron-peel, chicory, celery, parsley, cabbage leaves, Chinese cabbage leaves, radish leaves, red radish leaves, carrot leaves, spinach leaves, broccoli leaves, cauliflower leaves, ashitaba, dropwort leaves, Welsh onions, onions, leek leaves, crown daisies, marsh mallows, red leaf mustard, lettuces, aloes, radish, alfalfas, beet, asparaguses, kales, pak-choi, green mustards, red mustards, red chicory, new green (surname of leaf broccoli), *Angelica gigas*, butterburs, *Isodon jaonicus*, bean sprouts, rosemary, sages, and green teas to increase the content of diet fibers and to reinforce nutrients.

Preferably, the anti-obesity diet fibers composition further comprises one or more ingredient selected from the group consisting of dietary fiber of oatmeal, gum from the seed of psyllium, dietary fiber of chicory, powder of green tea extract, powder of orange-peel, powder of *Garcinia cambogia* extract, and powder of alfalfa.

These ingredients are known to contain many dietary fibers or to have effects on reducing weight and are used to more greatly increase the effects on reducing weight which the present invention intends to accomplish.

More preferably, the anti-obesity diet fibers composition further comprise one or more selected ingredient from the group consisting of taurine, L-carnitine, vitamin C, vitamin E, vitamin A, aspartame, xylitol, and oligosaccharides.

These ingredients are known to improve lipid metabolism or play roles of helping the other assistant nutrients.

The following powder comprising diet fibers was prepared for humans.

Dietary fibers of oatmeal 10 g, gum from seed of psyllium 10 g, dietary fibers of chicory 10 g, powder of persimmon leaves 20 g, powder of buckwheat leaves 20 g, powder of Chinese matrimony vine leaves 20 g, taurine 1 g, L-carnitine 1 g, vitamin C 1.7 g, vitamin E 0.3 g, vitamin A 0.5 g, aspartame 1 g, xylitol 2.5 g and oligosaccharides 2 g were mixed to prepare an anti-obesity diet fibers powder.

20 g of the prepared anti-obesity diet fibers powder was suspended in 200 cc of water to provide an anti-obesity diet fibers beverage.

After the diet fibers beverage was consumed in an amount of 200 cc per day for thirty days, blood was gathered and analyzed. In control groups, only water was consumed.

As a result, in comparison with the control group, the group administered the diet fibers beverage showed an average body fat decrease of 5%, an average serum cholesterol decrease of 8% and an average serum triglycerides decrease of 10%.

Therefore, good effects on reducing body fat can be expected when various kinds of plants leaves (vegetables, and powder of fruit peels) were consumed.

Example 10

Preparing Anti-Obesity Uncooked Food

The present invention provides an anti-obesity uncooked food composition which comprises one or more ingredient selected from the group consisting of powder of persimmon leaves, powder of buckwheat leaves, powder of Chinese matrimony vine leaves in 25 parts by weight, one or more cereals selected from the group consisting of powder of uncleaned rice, powder of barley, powder of oat, powder of parched beans, powder of parched sesames, and powder of peanuts in 35 parts by weight, one or more seaweeds selected from the group consisting of powder of kelp, powder of layer, and powder of brown seaweed in 5 parts by weight, one or more vegetables selected from the group consisting of powder of carrots, powder of onions, powder of garlic, powder of cabbage, powder of old pumpkins, powder of tomatoes, powder of broccoli, powder of spinach, powder of radish leaves, and powder of Chinese cabbage leaves in 10 parts by weight, one or more ingredient selected from the group consisting of chicory fibers, extract or powder of green teas, extract or powder of orange-peels, and extract or powder of plantains in 15 parts by weight and one or more ingredient selected from the group consisting of powder of shiitake mushrooms, extract of red peppers, extract of yeast, hydroxyl citric acid, taurine, L-carnitine, lecithin, and vitamin C in 10 parts by weight. This anti-obesity uncooked food makes it possible to provide essential nutrients and reduce weight at the same time. From the above-mentioned ingredients, carbohydrates, proteins, and fatty acids needed for providing nutrients can be obtained and inorganic salts, vitamins, and dietary fibers needed for health as assistant for nutrients also can be obtained.

To inspect the anti-obesity effects, the following composition was prepared and consumed in an amount of 80 g every day.

Powder of Chinese matrimony vine leaves 5 g, powder of buckwheat leaves 10 g, powder of persimmon leaves 10 g, powder of uncleaned rice 5 g, powder of barley 5 g, powder of oat 10 g, powder of parched beans 5 g, powder of parched sesames 5 g, powder of peanuts 5 g, powder of kelp 2 g, powder of layer 1.5 g, powder of brown seaweed 2 g, powder of carrots 1.0 g, powder of onions 1.0 g, powder of garlic 1.0 g, powder of cabbages 1.0 g, powder of old pumpkins 1.0 g, powder of tomatoes 1.0 g, powder of broccoli 1.0 g, powder of spinach 1.0 g, powder of radish leaves 1.0 g, and powder of Chinese cabbage leaves 1.0 g, chicory fibers 3.0 g, powder of green teas 3.0 g, powder of orange-peels 3.0 g, powder of ashitaba 2.0 g, powder of kale 2.0 g, powder of plantains 2.0 g, powder of shiitake mushrooms 1.0 g, extract of red peppers 1.0 g, extract of yeast 1.0 g, hydroxyl citric acid 2.0 g, taurine 3.0 g, L-carnitine 1.0 g, and lecithin 1.0 g were mixed to prepare an anti-obesity composition for uncooked food.

Each person consumed 40 g two times every day. After thirty days, the result of examination showed an average body fat decrease of 1.50 kg, an average serum total cholesterol decrease of 10% and an average serum triglycerides decrease of 10%.

Example 11

Producing Anti-Obesity Powder

The present invention provides compositions of powder for inhibiting obesity characterized by containing one or more ingredient selected from the group consisting of powder of persimmon leaves, powder of buckwheat leaves, and powder of Chinese matrimony vine leaves.

On the other hand, preferably, the compositions for the above powder for inhibiting obesity further comprise one or more ingredient selected from the group consisting of starch of wheat flour, starch of potatoes, starch of corns, starch of sweat potatoes, and starch of tapiocas. More preferably, the compositions for the above powder for inhibiting obesity further comprise one or more ingredient selected from the group consisting of powder of persimmon leaves, powder of buckwheat leaves, powder of Chinese matrimony vine leaves in an amount of 20-40 weight %, in addition to the starch powder in an amount of 60-80 weight %.

The powder produced by this method can be used to fry high-fat foods such as vegetable jerking, fish jerking, chicken jerking, and tempura etc. The powder for inhibiting obesity for fried chicken was produced by adding starches of wheat flour 40 g, starches of tapiocas 20 g, powder of persimmon leaves 20 g, and powder of buckwheat leaves 20 g.

Ten people consumed one piece of chicken's legs fried in oil for inhibiting obesity per day for thirty days and blood was gathered and analyzed. In control groups, chicken's legs fried produced using usual powder were used.

As a result, in comparison with the group which consumed chicken's legs fried using usual powder, the group which consumed chicken fried using anti-obesity powder showed a little weight decrease, and in the control group weight increased a little.

Example 12

Producing Anti-Obesity Processed Meat Products

Products such as hamburgers, hot dogs, sausages are high lipid raw materials for food, avoided by consumers because of the danger of heart disease, high blood lipid syndrome, and obesity.

An increase in body fat can be prevented by consuming meat processed foods produced by mixing anti-obesity powder of plant leaves described before 3-10%, other vegetable ingredients capable of improving lipid metabolism 10% and these raw materials for food 80%. For example, the inventors manufactured anti-obesity hamburgers as following. Flesh and meat such as chicken, duck, pork, mutton can also be used as meat for hamburger as well as beef.

Hamburgers were produced by thoroughly mixing beefs for hamburger (ground beef) 80 g, powder of persimmon leaves 3.0 g, powder of buckwheat leaves 3.0 g, powder of endive leaves 3.0 g, powder of onions 3 g, powder of carrots 2 g, powder of garlic 1 g, and powder of potatoes 5 g.

After the hamburgers were consumed in an amount of one per day, blood was tested and weight measurements were performed. The results showed that weight decreased (−1.0%) and serum lipid concentration decreased 2-5%.

Anti-obesity hot dogs and anti-obesity sausages can also be provided by a similar method.

Example 13

Producing Anti-Obesity Coffee

Because modern people's life is very busy, it will be very convenient that we can produce and drink tea or coffee containing ingredients which can improve lipid metabolism in our bodies and inhibit obesity.

Tea leaves abound in polyphenols, such as catechin, tannin, and caffeine etc., bioflavonoids and vitamins, such as vitamin C. Accordingly, in case of drinking enough abundant green teas, effects of improving lipid metabolism in our bodies may be accomplished. But, the total amount of materials effused from green tea is too small to show the effects of improving lipid metabolism.

Coffee beans comprise polyphenols such as 2,4 dihydroxycinnamic acid, tannin, and caffeine etc. and bioflavonoids, so that they may have effects on reducing cholesterol. But the amount of materials effused from coffee is too small to show effects.

The present inventors produced coffee compositions containing polyphenols or bioflavonoids, prepared powder of plant extracts containing polyphenols or bioflavonoids and produced coffee compositions containing the powder of plant extracts. The inventors then investigated the effects of the coffee compositions on improving lipid metabolism and inhibiting obesity.

Accordingly, an object of the present invention is to provide coffee compositions comprising polyphenols, bioflavonoids, or powder of plant extracts containing these materials for improving lipid metabolism and inhibiting obesity.

The coffee compositions of the present invention were produced by adding polyphenols, bioflavonoids, powder of plant extracts containing polyphenols or bioflavonoids, or substances promoting lipid metabolism to coffee powder. The coffee compositions reduced the accumulation of cholesterol and trigycerides in the body.

It is known that anti-oxidizing agents such as L-carnitine, vitamin C, vitamin E, and vitamin P, etc., promote lipid metabolism and a polypenol, sesamol in sesames is an anti-oxidation agent which helps lipid metabolism. Vitamin P is a methyl hesperidin and a bioflavonoid.

In the present invention, citric acids, hydroxyl citric acids, or taurine can be added as food additives to improve coffee taste.

The present inventors have studied materials which are anti-obesity and inhibit production of cholesterol from natural food materials and confirmed that polyphenols (for example, tannin, catechin, antocianoid) and bioflavonoids (for example, hesperidin, naringin, rutin, quercetin, cinnamic acid derivatives, etc.) had effects of anti-oxidizing, inhibiting cholesterol and triglycerides, promoting production of HDL cholesterol, and anti-obesity.

In the present invention, plants containing polyphenols or bioflavonoids comprise persimmon leaves, buckwheat leaves, Chinese matrimony vine leaves, green tea leaves, garlic, onions, carrots, grape-peels, orange (citron, tangerine, orange, lemon, and grapefruit)-peels, vegetables, fruits, and herbs, etc.

The coffee powder compositions were provided by mixing the polyphenols or bioflavonoids with coffee powder in pure form directly or by mixing the boiling water or ethanol extract powder from plants containing the materials with coffee powder. When the provided coffee powder was dissolved in hot water and consumed several times per day, the prevention of high blood lipid syndrome, stroke, and hypertension etc., the reduction of body fat and thereby obesity decrease are expected.

The preferable ratio of the coffee composition is coffee powder 10-50 weight %, polyphenols or bioflavonoids 1-10 weight %, powder of plant extracts containing polyphenols or bioflavonoids 10-40 weight %, and food additive 10-40 weight %.

To produce the anti-obesity coffee compositions containing polyphenols or bioflavonoids, persimmon leaves, buckwheat leaves, and Chinese matrimony vine leaves were extracted by water at 100° for four hours. The extracts were concentrated under reduced pressure and lyophilized, to prepare powders of each plant extract. The extracts of green tea, the powder of orange-peel extracts were purchased from Hang Rim pharmaceutical company in Korea.

The powder of plant extracts produced was used to prepare a coffee composition of the following ratio.

TABLE 10

The constitution of coffee compositions containing powder of plant extracts

| Ingredients | Composition ratio (%) |
| --- | --- |
| Coffee Powder | 40 |
| Powder of persimmon leaves extracts | 20 |
| Powder of buckwheat leaves extracts | 10 |
| Powder of green tea extracts | 10 |
| Powder of orange-peel leaves extracts | 10 |
| L-carnitine | 3 |
| Taurine | 5 |
| Vitamin C | 2 |
| Total | 100(%) |

To investigate the effects of the coffee composition of the present invention on improving lipid metabolism and inhibiting obesity, the prepared coffee composition 5.0 g was dissolved into a cup of hot water (about 150 cc) and was consumed. A total of 15 g was consumed once after eating breakfast, lunch, and dinner respectively, three times per day.

The change of weight was recorded every day. In a month, after a blood test was performed, the amount of total cholesterol, triglycerides, HDL, and LDL were measured.

The results showed body weight decreased 1.5%, total cholesterol decreased 10% and triglycerides decreased 8%.

Example 14

Producing Anti-Obesity Carbohydrates Food

In recent years, many people believe that materials that cause obesity are excess carbohydrates such as starch, glucose, sucrose etc. Accordingly, many people try to abstain from consuming meat and carbohydrate foods and to abundantly consume fish, fruits, and vegetables, etc.

Spreading of this recognition is going to inhibit consumption of carbohydrate foods and processed meat products. However, when the function of carbohydrate foods and processed meat products is improved by adding polyphenols and bioflavonoids from edible plants, plant powder or plant extract containing a lot of those substances, consumers can enjoy carbohydrate foods safely and obesity can be prevented.

We have many problems in our country because we can't adjust supply and consumption of agricultural products. Sometimes vegetables, such as spinach, garlic, red peppers, onions, Chinese cabbage, cabbage, and radishes, etc., and fruits such as oranges, apples, pears, and grapes, etc., are so scarce that we suffer from importation. Other times they are so abundant that farmers have to plow and overturn fields because the price is lower than the production price, so that we feel sorry.

There are rice, barley, wheat, corn, potato, and sweet potato, etc., as common starch materials among agricultural products. Powder of rice, powder of barley, powder of wheat, powder of corn, powder of potato, and powder of sweet potato, etc., extracted from these grains are used as raw materials for main foods such as boiled rice, noodles, Chinese noodles, spaghetti, bread, cakes, confectionery, pizza peels, bun peels, cereals, candies, and snacks, etc.

In cases where these materials are abundantly mixed with plant ingredients of plant powder containing polyphenols or bioflavonoids, which will improve lipid metabolism and inhibit obesity, we can develop anti-obesity products and consumer's interest will increase.

The present inventors produced anti-obesity edible powder or extracts abundantly containing polyphenols or bioflavonoids and added the produced plant powder or extract to powder of rice, powder of corn starch, powder of potato starch, powder of sweet potato starch, powder of tapioka starch or powder of wheat to try to develop carbohydrate foods that can improve various kinds of lipid metabolism and be used for anti-obesity. Several examples will be described below.

In the present invention, preferably, the starch powder is one or more ingredient selected from the group consisting of powder of rice, powder of barley, powder of corn starch, powder of potato starch, powder of sweet potato starch, powder of tapioka starch and powder of wheat. In the present invention, anti-obesity plant materials comprise powder of persimmon leaves, powder of buckwheat leaves, powder of Chinese matrimony vine leaves and powder of endive leaves and powder of these plant extracts.

In addition, preferably, plants for improving taste and providing vitamins are one or more ingredients selected from the group consisting of sesame, jujube, carrot, old pumpkin, dried grape, Welsh onion, onion, garlic, red pepper, cabbage, Chinese cabbage, radish leaves, green tea leaves, eggplant, celery, broccoli, cauliflower, tomato, and spinach.

The forms of carbohydrate foods manufactured using the present food materials is preferably one selected among noodles, Chinese noodles, knife-cut noodles, Udong, spaghetti, bun peels, bread, confectionery, pizza peels, cereals, candies, and snacks, etc.

A. Method for Producing Noodles Made from Powder of Wheat:

Powder of persimmon leaves 50 g, powder of chicory leaves 50 g, water 700 cc, and salt 2% were added to powder of wheat 1000 g, and kneaded. From this, noodles were pulled out in a noodle machine and were dried by wind.

B. Method for Producing Noodles from Powder of Rice

Powder of persimmon leaves 100 g, water 700 cc, and salt 2% were added to powder of rice 1000 g, and kneaded. From this, noodles were pulled out in a noodle machine and were dried by wind.

C. Method for Producing Udong Noodles:

Udong noodles were produced by adding powder of green tea leaves 50 g, boiling water extract of orange-peels 50 g, powder of persimmon leaves 100 g, powder of buckwheat leaves 100 g, powder of Chinese matrimony vine leaves 100 g, powder of endive leaves 100 g, powder of onions 100 g, powder of garlic 100 g, powder of carrots 100 g, water 1000 cc, and salt 2% to powder of wheat 2,300 g. Udong noodles were consumed in an amount of 150 g every day. From the results, weight decreased 2.0 kg (−2.5%), serum cholesterol decreased 10%, and serum triglycerides decreased 10%.

Example 15

Producing Anti-Obesity Beverage

Powder of boiling water extract of plant leaves comprising anti-obesity ingredients, was produced according to Examples 1 and 2. For example, after it was identified that extracts of persimmon leaves, extracts of buckwheat leaves, and extracts of Chinese matrimony vine leaves inhibited increase of animals' weight, they were used for producing anti-obesity beverages.

Diet beverages were produced by adding plant extracts containing ingredients improving lipid metabolism and prohibiting obesity to water, carbonic acid drinks, fruit juices, and healthy drinks, etc. To improve taste and perfume, additionally, aspartame 0.1%, xylitol 0.5-5%, fructooligosaccharide 1-5%, taurine 1-4%, and vitamin C 0.1-0.5% can be added selectively. To obtain anti-obesity effects, extracts of persimmon leaves and buckwheat leaves can be added in the beverages to 0.5-10%.

A. For example, anti-obesity orange juice was produced by mixing 90 g of orange juice, 5 g of persimmon leaves extracts, 0.1 g of aspartame, 1 g of vitamin C, and 3.9 g of taurine.

B. Various kinds of beverages can be produced by adding orange-peel extracts 3%, and green tea extracts 3% to improve lipid metabolism.

C. Producing anti-obesity bean beverages.

Bean beverages were produced by adding 20 g of bean protein decomposed by enzyme, 5 g of persimmon leaves extracts 5 g, 1 g of aspartame, 4 g of fructooligosaccharide, and 100 mL of water.

Example 16

Producing Kimchi for Reducing Weight

A. Producing Chinese Cabbage Kimchi for Reducing Weight.

First, salted cabbages were prepared by placing Chinese cabbages 2000 g in water 3000 g and salt 200 g, preserving them with salt for 8 hours, and then washing them.

To mix with the salted cabbages, elementary dressing materials were prepared by mixing boiled gruel prepared by placing powder of wheat 30 g in water 500 g, powder of red peppers 110 g, radish cut into small pieces 250 g, ginger 29 g, Welsh onions 104 g, dried powder of onions 4 g, dried powder of garlic 12 g, and salted anchovies 200 g.

In the control group, usual Chinese cabbage Kimchi was produced by placing the above dressing materials between Chinese cabbage leaves, placing in Kimchi bottles, and then fermenting at room temperature for 4 days.

On the other hand, to produce Kimchi for reducing weight, powder of persimmon leaves 40 g, powder of persimmon leaves 80 g, or 'powder of persimmon leaves 20 g+powder of buckwheat leaves 20 g+powder of Chinese matrimony vine leaves 20 g' were placed in the dressing materials, which were placed between the salted cabbage leaves 2000 g and then fermented at room temperature for 4 days according to the above method.

In four days, taste was compared, so that the control group (usual Chinese cabbage Kimchi) and the Chinese cabbage Kimchi in which was placed powder of persimmon leaves 40 g, tasted good and secondly, that in which was placed 'powder of persimmon leaves 20 g+powder of buckwheat leaves 20 g+powder of Chinese matrimony vine leaves 20 g', also tasted good.

On the other hand, the comparison of the taste was a result obtained through the examination of senses, wherein ten staff members were selected for examination among skillful panels having experience in the examination of senses. The examination [grade] marks are awarded according to the following criteria: In comparison with the control group, very good was 5 points, good was 4 points, fair was 3 points, poor was 2 points, and very poor was 1 point.

The results showed that the Chinese cabbage Kimchi in which was placed powder of persimmon leaves 40 g was average 4.20 points; that in which was placed 'powder of persimmon leaves 20 g+powder of buckwheat leaves 20 g+powder of Chinese matrimony vine leaves 20 g' was average 3.95 points; and that in which was placed the powder of persimmon leaves 40 g was average 3.70 points.

Ten people consumed the Chinese cabbage Kimchi in which was placed powder of diet fiber of persimmon leaves 40 g per the Kimchi produced by the method 1000 g in an amount of 150 g per day (each time 75 g, two times per day)(the experimental group). In the control group, people consumed Kimchi in which powder of diet fiber of persimmon leaves was not placed.

In thirty days, the result of measuring body fat, weight, the amount of serum cholesterol, and the amount of serum triglycerides showed the effects that in the experimental group, body fat and weight decreased 1.5%, serum cholesterol decreased 8%, and serum triglycerides decreased 10%. But, in the control group, there was little difference in comparison with those before experimentation.

B. Producing Radish Leaf Kimchi for Reducing Weight.

Radish leaf Kimchi was produced according to the following method.

First, salted radish leaves were prepared by placing radish leaves 2000 g in water 3000 g and salt 200 g, preserving them with salt for 8 hours, and then washing them.

To mix with the salted radish leaves, elementary dressing materials were prepared by mixing boiled gruel prepared by placing powder of wheat 30 g in water 500 g, powder of red peppers 110 g, ginger 29 g, Welsh onions 104 g, dried powder of onions 4 g, dried powder of garlic 12 g, and salted anchovies 200 g.

In the control group, usual radish leaf Kimchi was produced by mixing the above dressing materials with radish leaves, placing in Kimchi bottles, and then fermenting at room temperature for 4 days.

On the other hand, to produce radish leaf Kimchi for reducing weight, powder of persimmon leaves 40 g, powder of persimmon leaves 80 g, or 'powder of persimmon leaves 20 g+powder of buckwheat leaves 20 g+powder of Chinese matrimony vine leaves 20 g' were placed in the dressing materials, which were mixed with the salted radish leaves 2000 g, and then fermented at room temperature for 4 days according to the above method.

In four days, the taste was compared, so that the control group (usual radish leaf Kimchi) and the radish leaf Kimchi in which was placed powder of persimmon leaves 40 g, tasted good and secondly, that in which was placed 'powder of persimmon leaves 20 g+powder of buckwheat leaves 20 g+powder of Chinese matrimony vine leaves 20 g', also tasted good.

On the other hand, the comparison of the taste was a result obtained through the examination of senses, wherein ten staff members were selected for examination among skillful panels having experience in the examination of senses. The examination [grade] marks are awarded according to the following criteria: In comparison with the control group, very good was 5 points, good was 4 points, fair was 3 points, poor was 2 points, and very poor was 1 point.

The results showed that the radish leaf Kimchi in which was placed powder of persimmon leaves 40 g was average 4.33 points; that in which was placed 'powder of persimmon leaves 20 g+powder of buckwheat leaves 20 g+powder of Chinese matrimony vine leaves 20 g' was average 4.05 points and that in which was placed the powder of persimmon leaves 40 g was average 3.88 points.

C. Producing Leaf Mustards Kimchi for Reducing Weight.

Leaf mustards Kimchi was produced according to the following method.

First, salted leaf mustards were prepared by placing leaf mustards 2000 g in water 3000 g and salt 200 g, preserving them with salt for 8 hours, and then washing them.

To mix with the salted leaf mustards, elementary dressing materials were prepared by mixing boiled gruel prepared by placing powder of wheat 30 g in water 500 g, powder of red peppers 110 g, ginger 29 g, Welsh onions 104 g, dried powder of onions 4 g, dried powder of garlic 12 g, and salted anchovies 200 g.

In the control group, usual leaf mustards Kimchi was produced by mixing the above dressing materials with leaf mustards, placing in Kimchi bottles, and then fermenting at room temperature for 4 days.

On the other hand, to produce leaf mustards Kimchi for reducing weight, powder of persimmon leaves 40 g, powder of persimmon leaves 80 g, or 'powder of persimmon leaves 20 g+powder of buckwheat leaves 20 g+powder of Chinese matrimony vine leaves 20 g' were placed in the dressing materials, which were mixed with the salted leaf mustards 2000 g, and then fermented at room temperature for 4 days according to the above method.

In four days, taste was compared, so that the control group (usual leaf mustards Kimchi) and the leaf mustards Kimchi in which was placed powder of persimmon leaves 40 g, tasted good and secondly, that in which was placed 'powder of persimmon leaves 20 g+powder of buckwheat leaves 20 g+powder of Chinese matrimony vine leaves 20 g', also tasted good.

On the other hand, the comparison of the taste was a result obtained through the examination of senses, wherein ten staff members were selecteds for examination among skillful panels having experience in the examination of senses. The examination [grade] marks are awarded according to the following criteria: In comparison with the control group, very good was 5 points, good was 4 points, fair was 3 points, poor was 2 points, and very poor was 1 point.

The results showed that the leaf mustards Kimchi in which was placed the powder of persimmon leaves 40 g was average 4.15 point; that in which was placed 'the powder of persimmon leaves 20 g+the powder of buckwheat leaves 20 g+the powder of Chinese matrimony vine leaves 20 g' was average 4.05 point; and that in which was placed the powder of persimmon leaves 40 g was average 3.68 point.

D. Producing Cabbage Kimchi for Reducing Weight.

Cabbage Kimchi was produced according to the following method.

Cabbages 2000 g were washed by water, and to mix with the cabbages, elementary dressing materials were prepared by mixing boiled gruel prepared by placing powder of wheat 30 g in water 500 g, powder of red peppers 110 g, radish cut into small pieces 250 g, ginger 29 g, Welsh onions 104 g, dried powder of onions 4 g, and dried powder of garlic 12 g, In the control group, usual cabbage Kimchi was produced by mixing the above dressing materials with cabbage, placing in Kimchi bottles, and then fermenting at room temperature for 4 days.

On the other hand, to produce cabbage Kimchi for reducing weight, powder of persimmon leaves 40 g, powder of persimmon leaves 80 g, or 'powder of persimmon leaves 20 g+powder of buckwheat leaves 20 g+powder of Chinese matrimony vine leaves 20 g' were placed in the dressing materials, and the dressing materials were mixed with the cabbages 2000 g, and then fermented at room temperature for 4 days according to the above method.

In four days, taste was compared, so that the control group (usual leaf mustards Kimchi) and the leaf mustards Kimchi in which was placed powder of persimmon leaves 40 g, tasted good and secondly, the Kimchi in which was placed 'powder of persimmon leaves 20 g+powder of buckwheat leaves 20 g+powder of Chinese matrimony vine leaves 20 g', also tasted good.

On the other hand, the comparison of the taste was a result obtained through the examination of senses, wherein ten staff members were selected for examination among skillful panels having experience in the examination of senses. The examination [grade] marks are awarded according to the following: In comparison with the control group, very good was 5 points, good was 4 points, fair was 3 points, poor was 2 points, and very poor was 1 point.

The results showed that the cabbage Kimchi in which was placed the powder of persimmon leaves 40 g was average 3.97 point; that in which was placed the powder of persimmon leaves 20 g+the powder of buckwheat leaves 20 g+the powder of Chinese matrimony vine leaves 20 g', was average 3.72 point; and that in which was placed the powder of persimmon leaves 40 g was average 3.55 point.

E. Producing Buckwheat Leaf Kimchi for Reducing Weight.

Buckwheat leaf Kimchi was produced according to the following method.

First, salted buckwheat leaves were prepared by placing buckwheat leaves 2000 g in water 3000 g and salt 200 g, preserving them with salt for 2 hours, and then washing them. To mix with the salted buckwheat leaves, elementary dressing materials were prepared by mixing boiled gruel prepared by placing powder of wheat 30 g in water 500 g, powder of red peppers 110 g, ginger 29 g, Welsh onions 104 g, dried powder of onions 4 g, dried powder of garlic 12 g, and salted anchovies 200 g.

The dressing materials were mixed with the salted buckwheat leaves, and then fermented at room temperature for 4 days according to the above method.

Ten people consumed the buckwheat leaf Kimchi for reducing weight produced by the above method in an amount of 150 g per day (each time 75 g, two times per day)(the experimental group). In the control group, people consumed the usual buckwheat leaf Kimchi.

In thirty days, the result of measuring body fat, weight, the amount of serum cholesterol, and the amount of serum triglycerides showed the effects that in the experimental group, body fat and weight decreased 2%, serum cholesterol decreased 2%, and serum triglycerides decreased 15%. But, in the control group, there was little difference in comparison with those before experiment.

E. Producing Chinese Matrimony Vine Leaf Kimchi for Reducing Weight.

Chinese matrimony vine leaf Kimchi was produced according to the following method.

First, salted Chinese matrimony vine leaves were prepared by placing Chinese matrimony leaves 2000 g in water 3000 g and salt 200 g, preserving them with salt for 2 hours, and then washing them. To mix with the salted Chinese matrimony vine leaves, elementary dressing materials were prepared by mixing boiled gruel prepared by placing powder of wheat 30 g in water 500 g, powder of red peppers 110 g, ginger 29 g, Welsh onions 104 g, dried powder of onions 4 g, dried powder of garlic 12 g, and salted anchovies 200 g.

The dressing materials were mixed with the salted Chinese matrimony vine leaves, and then fermented at room temperature for 4 days according to the above method.

Ten people consumed the Chinese matrimony vine leaf Kimchi for reducing weight produced by the above method in an amount of 150 g per day (each time 75 g, two times per day)(the experimental group). In the control group, people consumed the usual Chinese matrimony vine leaf Kimchi.

In thirty days, the result of measuring body fat, weight, the amount of serum cholesterol, the amount of serum triglycerides showed the effects that in the experimental group, body fat and weight decreased 1.5%, serum cholesterol decreased 10%, and serum triglycerides decreased 10%. But, in the control group, there was little difference in comparison with those before experiment.

Example 17

Producing Anti-Obesity Herb Tea and Anti-Obesity Green Tea

The present inventors have made every effort to develop plant leaves having the excellent anti-obesity effect and to develop anti-obesity herb tea and anti-obesity green tea using this. It was thus found that persimmon leaves, buckwheat leaves, and Chinese matrimony vine leaves had the anti-obesity effect and the inventors accomplished the present invention by producing anti-obesity powder of herb tea, anti-obesity powder of green tea, and beverages made from these.

Therefore, an object of the present invention is to provide anti-obesity powder of herb tea, anti-obesity powder of green tea, and beverages made from these.

To accomplish the above object, the present invention provides anti-obesity powder compositions of herb tea containing one or more ingredient selected from the group consisting of powder of persimmon leaves, powder of buckwheat leaves, and powder of Chinese matrimony vine leaves and herb tea beverage from them.

Also, the present invention provides anti-obesity powder compositions of green tea containing one or more ingredient selected from the group consisting of powder of persimmon leaves, powder of buckwheat leaves, and powder of Chinese matrimony vine leaves and green tea beverage and green tea beverage from them.

The present invention provides the anti-obesity powder compositions of herb tea characterized by adding one or more ingredient selected from the group consisting of powder of persimmon leaves, powder of buckwheat leaves, and powder of Chinese matrimony vine leaves which have the effects on improving lipid metabolism and reducing weight to powder compositions of herb tea.

On the other hand, preferably, the above powder compositions of herb tea further contain one or more ingredient selected from the group consisting of perfume of rosemary extracts, perfume of sage extracts, and perfume of rose extracts.

More preferably, the said anti-obesity powder compositions of herb tea further contain powder of chicory leaves, which has been known as materials having the effect on reducing weight up to now and play roles of promoting the effect on reducing weight in the present invention.

Also, preferably, in the above anti-obesity powder compositions of herb tea, the ratio, at which reducing weight and sensual beauty are most excellent, of ingredients is the following:

one or more ingredients selected from the group consisting of powder of persimmon leaves, powder of buckwheat leaves, and powder of Chinese matrimony vine leaves in 65 parts by weight, powder of chicory leaves in 30 parts by weight, and one ingredient selected from the group consisting of perfume of rosemary extracts, perfume of sage extracts, and perfume of rose extracts in 5 parts by weight. More preferably, the above one or more ingredients selected from the group consisting of powder of persimmon leaves, powder of buckwheat leaves, and powder of Chinese matrimony vine leaves added in 65 parts by weight comprises powder of persimmon leaves in 25 parts by weight, powder of buckwheat leaves in 20 parts by weight, and powder of Chinese matrimony vine leaves in 20 parts by weight, respectively.

The above powder is produced to final goods by placing in a teabag. And in the case of using a teabag, the tea is consumed by placing the teabag in hot water and gathering the extracts.

Also, the present invention provides anti-obesity powder compositions of green tea characterized by adding one or more ingredients selected from the group consisting of powder of persimmon leaves, powder of buckwheat leaves, and powder of Chinese matrimony vine leaves which have the effects on improving lipid metabolism and reducing weight to powder compositions of green tea.

Preferably, the above anti-obesity powder compositions of green tea comprise one or more ingredient selected from the group consisting of powder of persimmon leaves and powder of buckwheat leaves in 50 parts by weight and powder of green tea leaves in 50 parts by weight, more preferably, above one or more selected from a group consisting of powder of persimmon leaves and powder of buckwheat leaves added as much as in 50 parts by weight comprises powder of persimmon leaves in 30 parts by weight and powder of buckwheat leaves in 20 parts by weight, respectively.

On the other hand, preferably, the size of powder of persimmon leaves, powder of buckwheat leaves, and powder of Chinese matrimony vine leaves added to the above anti-obesity powder compositions of herb tea and to the above anti-obesity powder compositions of green tea is 0.5-1.5 mm long. This is due to the fac that in this size, when they are extracted in tea, the approach of solvent water is excellent, so that available ingredients can be extracted best.

Also, the present invention provides anti-obesity herb tea beverage, anti-obesity coffee beverage, and anti-obesity green tea beverage characterized by containing boiling water extracts prepared by extracting with hot water from the present invention, anti-obesity powder of herb tea and to anti-obesity powder of green tea. The process of extracting with hot water and producing beverage is practiced in accordance with usual methods.

Also, the present invention provides anti-obesity herb tea beverage and anti-obesity green tea beverage characterized by containing herb tea solution and green tea solution produced by powdering boiling water extracts of the above anti-obesity powder compositions of herb tea and anti-obesity powder compositions of green tea, dissolving them in water. The process of powdering the boiling water extracts and dissolving them in water is practiced in accordance with usual methods.

A. Producing Anti-Obesity Powder Compositions of Herb Tea.

After 1.0 mm size powder of persimmon leaves 25 g, 1.0 mm size powder of buckwheat leaves 20 g, and 1.0 mm size powder of Chinese matrimony vine leaves 20 g, powder of chicory 30 g, and perfume of rosemary 5 g were mixed, products were produced by placing them 2.0 g in teabags respectively.

Boiling water extracts (herb tea) produced by adding hot water (80°, 15 L) to the anti-obesity powder compositions of herb tea 1,800 g were administered to ten people in an amount of 450 ml per day for thirty days respectively. After that time, blood was extracted and analyzed. The results showed that average weight decreased 0.6 kg, average body fat decreased 0.5 kg, average total cholesterol decreased 5%, and average total triglycerides decreased 7%.

B. Producing Anti-Obesity Powder Compositions of Green Tea.

After 1.0 mm size powder of persimmon leaves 30 g, powder of buckwheat leaves 20 g, and powder of green tea leaves 50 g were mixed, products were produced by placing them 2.0 g in teabags respectively.

Ten people were administered boiling water extracts (green tea) prepared by adding hot water (80°, 15 L) to the anti-obesity powder compositions of green tea produced above 1,800 g in an amount of 450 ml per day for thirty days respectively. After that time, blood was extracted and analyzed. The results showed that average weight decreased 0.5 kg, average body fat decreased 0.5 kg, average total cholesterol decreased 5%, and average total triglycerides decreased 6%.

Example 18

Producing Anti-Obesity Vegetable Beverages, Vegetable Soups, Vegetable Sauces, and Vegetable Salads Vegetable beverages, vegetable soups, and vegetable sauces were produced by grinding various vegetables such as cabbage, eggplant, carrot, garlic, leek, dropwort, broccoli, cauliflower, ginger, spinach, onion, tomato, alfalfa, pumpkin, strawberry, ashitaba, kale, asparagus, lettuce, parsley, celery, Chinese cabbage, radish, and green bean sprouts, etc. Vegetable salads are produced by properly mixing the above materials and dressing sauces. Anti-obesity vegetable beverages, vegetable soups, vegetable sauces, and vegetable salads can be prepared by properly mixing anti-obesity materials explained in Examples 1, 2 and 3.

A. Producing Anti-Obesity Vegetable Beverages

In the case of improving taste by mixing anti-obesity vegetable extracts with vegetable juices, anti-obesity vegetable beverages can be obtained.

Buckwheat leaves or persimmon leaves 5 g
Powder of various kinds of vegetable extracts 20 g
Aspartame 0.1-0.2 g
Water 100 ml B. Producing Anti-Obesity Vegetable Soups.

The present invention provides powder compositions of anti-obesity vegetable soups using powder of persimmon leaves, powder of buckwheat leaves, or powder of Chinese matrimony vine leaves that have the effects on improving lipid metabolism and reducing weight.

According to the present invention, powder compositions of anti-obesity vegetable soups produced by adding one or more ingredient selected from the group consisting of powder of persimmon leaves, powder of buckwheat leaves, or powder of Chinese matrimony vine leaves to usual powder bases of vegetable soups may be produced. And, to relieve bitter tastes according to adding persimmon leaves or buckwheat leaves and to improve anti-obesity effect, powder bases of vegetable soups produced by mixing powder of Korean solomon seal, powder of endive leaves, powder of starches, powder of garlic, powder of onions, powder of ginger, powder of red peppers or peppers, powder of carrots, powder of Chinese cabbage leaves, powder of radish leaves, powder of cabbage leaves, taurine, powder of sesames and salt instead of usual powder bases of vegetable soups may be used.

At last, preferably, powder compositions of vegetable soups composed of one or more ingredient selected from the group consisting of powder of persimmon leaves, powder of buckwheat leaves, and powder of Chinese matrimony vine leaves, one or more ingredient selected from the group consisting of powder of Korean solomon seal, powder of chicory, powder of starches, powder of garlic, powder of onions, powder of ginger, powder of red peppers or peppers, powder of carrots, powder of Chinese cabbage leaves, powder of radish leaves, powder of cabbage leaves, and other kinds of vegetable, taurine, powder of sesames and salt are good.

The above materials were considered and were selected to relieve the neutral and physical characteristic of the powder of vegetable soups and bitter taste originated from persimmon leaves and buckwheat leaves added as main materials.

On the other hand, it is preferable that powder compositions of anti-obesity vegetable soups is composed of one or more ingredient selected from the group consisting of powder of persimmon leaves or powder of buckwheat leaves 33.4 weight %, powder of Korean solomon seal 3.3 weight %, powder of chicories 3.3 weight %, powder of starches 27 weight %, garlic 3.3 weight %, onions 3.3 weight %, gingers 1.3 weight %, powder of red peppers or peppers 3.3 weight %, carrots 3.3 weight %, powder of Chinese cabbage leaves 3.3 weight %, powder of radish leaves 3.3 weight %, the powder of cabbage leaves 3.3 weight %, taurine 3.3 weight %, powder of sesames 4 weight % and salt 1.3 weight %.

B. Producing Anti-Obesity Vegetable Sauces.

Sauce is the term that we call collectively spices of liquid or half fluid put in or sprinkled on food to bring out taste or color.

Anti-obesity compositions of tomato ketchup were provided as anti-obesity vegetable sauces.

Anti-obesity compositions of tomato ketchup are produced by adding one or more ingredient selected from the group consisting of powder of persimmon leaves, powder of buckwheat leaves, and powder of Chinese matrimony vine leaves. To relieve bitter tastes according to adding persimmon leaves or buckwheat leaves, the bases of tomato ketchup composed of the tomato pastes, powder of garlic, powder of onions, powder of carrots and other vegetable powder enumerated before and sucrose had is used.

On the other hand, it is preferable that anti-obesity compositions of tomato ketchup are composed of one or more ingredient selected from the group consisting of powder of persimmon leaves, powder of buckwheat leaves, and powder of Chinese matrimony vine leaves 20 weight %, tomato pastes 60 weight %, powder of garlic, powder of onions, powder of carrots and other vegetable powder 15 weight %, and sucrose 5%.

Anti-obesity compositions of spaghetti sauces are produced by adding one or more ingredient selected from the group consisting of powder of persimmon leaves, powder of buckwheat leaves, and powder of Chinese matrimony vine leaves. To relieve bitter tastes according to adding persimmon leaves, buckwheat leaves, and powder of Chinese matrimony vine leaves, bases of spaghetti sauces composed of the tomato pastes, powder of garlic, powder of onions, powder of carrots, powder of red peppers or peppers, and sucrose is used.

At last, preferably, anti-obesity compositions of spaghetti sauces composed by mixing one or more ingredient selected from the group consisting of powder of persimmon leaves, powder of buckwheat leaves, and powder of Chinese matrimony vine leaves 20 weight %, tomato pastes 60 weight %, powder of garlic, powder of onions, powder of carrots and powder of red peppers or peppers 15 weight %, and sucrose 5% are good.

E. Producing Vegetables Salads.

Anti-obesity vegetables salads can be produced by mixing persimmon leaves, buckwheat leaves, Chinese matrimony vine leaves, endive leaves, and extracts of these with various kinds of vegetables, meat, and beans, etc. For example, anti-obesity vegetables salads can be produced by selectively choosing kinds of vegetable, such as lettuce, celery, radish shoot, alfalfa, onion, pimento, tomato, pineapple, carrot, cucumber, green been, Chinese cabbage, cabbage, chicory, endive, spinach, broccoli, cauliflower, artichoke, cresson, radish, crown daisy, parsley, boiled bean, boiled corn, olive, and boiled potato etc. 60-70 g, anti-obesity vegetables ingredients explained above 10-20 g, and salad sauces 10-20 g to give taste.

Anti-obesity vegetables salads can be produced according to the above method, but tuna salads, chicken salads, salmon salads, cheese salads, and egg salads, etc., can be produced especially by mixing vegetables ingredients 30-40 g, boiled chicken, smoked salmon, cheese, or boiled egg, etc., 20-30 g, anti-obesity vegetables ingredients 10-20 g, and salad sauces 10-20 g.

Example 19

Producing Anti-Obesity Milk Products

The anti-obesity plant extracts shown in Examples 1, 2 and 3 were used for producing milk, cheese, yogurt, and ice cream, etc.

Milk, cheese, yogurt, and ice cream can contribute to increasing body fat because they occasionally have a lot of lipid components. To relieve this nature, anti-obesity milk, cheese, yogurt, and ice cream, etc., are produced by mixing with extracts of persimmon leaves, extracts of buckwheat leaves, extracts of Chinese matrimony vine leaves, extracts of green tea and endive leaves, etc., in amounts of about 1-10% when the products were produced.

Example 20

Producing Anti-Obesity Alcoholic Drinks

A large cause of obesity is excessive intake of excessive alcoholic drinks, excessive intake of starchy food, and excessive intake of high lipid meat.

To relieve this nature, anti-obesity alcoholic drinks can be produced by mixing one or more ingredients selected from the group consisting of persimmon leaves extracts, buckwheat leaves extracts, and Chinese matrimony vine leaves extracts indicated in Examples 1, 2, 3, and 4 etc., in amounts of about 0.1-5% with various kinds of alcoholic liquors.

For example, increase of weight can be inhibited when persimmon leaf extracts 5 g are mixed with distilled liquor 370 ml and consumed.

Example 21

Producing Anti-Obesity Gums

Anti-obesity Gums for reducing serum cholesterol can be produced by adding the plant extracts shown in Examples 1, 2 and 3 to gums. In the case of using gums produced by mixing extracts of orange-peel and extracts of green tea with extracts of persimmon leaves, extracts of buckwheat leaves, or extracts of Chinese matrimony vine leaves at a proper rate (1:1:1) and placing them in amounts of 0.1-10% in gums, the effects on reducing body fat or improving lipid metabolism can be obtained.

INDUSTRIAL APPLICABILITY

As described above, the compositions according to the present invention have excellent effects on the reduction of weight of animals or humans without side effects. Thus, the present compositions have prominent effects on the health food industry.

What is claimed is:

1. An anti-obesity composition, comprising, as active ingredients,
    persimmon leaf powder,
    an aqueous extract of persimmon leaves, wherein the persimmon leaves are extracted with boiling water,
    buckwheat leaf powder,
    an ethanol extract of buckwheat leaves,
    an aqueous extract of buckwheat leaves, wherein the buckwheat leaves are extracted with boiling water,
    buckwheat flower powder,
    an ethanol extract of buckwheat flowers,
    an aqueous extract of buckwheat flowers, wherein the buckwheat flowers are extracted with boiling water,
    Chinese matrimony vine leaf powder,
    an ethanol extract of Chinese matrimony vine leaves,
    an aqueous extract of Chinese matrimony vine leaves, wherein the Chinese matrimony vine leaves are extracted with boiling water,
    endive leaf powder,
    an ethanol extract of endive leaves, and
    an aqueous extract of endive leaves, wherein the endive leaves are extracted with boiling water.

2. The anti-obesity composition of claim 1, further comprising:
    at least one dried and ground ingredient selected from the group consisting of:
    red pepper leaf,
    ripe cowpea leaf,
    bean leaf,
    barley leaf,
    wheat leaf,
    oat leaf,
    orange peel,
    citron peel,
    chicory,
    celery,
    parsley,
    cabbage leaf,
    Chinese cabbage leaf,
    radish leaf,
    red radish leaf,
    carrot leaf,
    spinach leaf,
    broccoli leaf,
    cauliflower leaf,
    ashitaba,
    dropwort leaf,
    Welsh onion,
    onion,
    leek leaf,
    crown daisies,
    marsh mallow,
    red leaf mustard,
    lettuce,
    aloe,
    alfafa,
    beet,
    asparagus,
    kale,
    pak-choi,
    green mustard,
    red mustard,
    red chicory,
    leaf broccoli,
    *Angelica gigas*,
    butterbur,

*Isodon japonicus*,
bean sprout,
rosemary,
sage, and
green tea.

3. The anti-obesity composition according to claim 2, which further comprises:
at least one ingredient selected from the group consisting of:
oatmeal fiber,
psyllium seed gum,
chicory fiber,
Korean Solomon seal root powder,
green tea extract powder,
orange peel powder,
*Garcinia cambogia* extract powder, and
alfafa powder.

4. The anti-obesity composition according to claim 3, which further comprises:
at least one ingredient selected from the group consisting of:
lecithin,
taurine,
L-carnitine,
vitamin C,
vitamin E,
vitamin A,
aspartame,
xylitol, and
oligosaccharides.

5. An anti-obesity composition, comprising:
a)
persimmon leaf powder,
an ethanol extract of persimmon leaves,
an aqueous extract of persimmon leaves, wherein the persimmon leaves are extracted with boiling water,
buckwheat leaf powder,
an ethanol extract of buckwheat leaves,
an aqueous extract of buckwheat leaves, wherein the buckwheat leaves are extracted with boiling water,
buckwheat flower powder,
an ethanol extract of buckwheat flowers,
an aqueous extract of buckwheat flowers, wherein the buckwheat flowers are extracted with boiling water,
Chinese matrimony vine leaf powder,
an ethanol extract of Chinese matrimony vine leaves,
an aqueous extract of Chinese matrimony vine leaves, wherein the Chinese matrimony vine leaves are extracted with boiling water,
endive leaf powder,
an ethanol extract of endive leaves,
an aqueous extract of endive leaves, wherein the endive leaves are extracted with boiling water,
ginseng powder,
an ethanol extract of ginseng, and
an aqueous extract of ginseng, wherein the ginseng is extracted with boiling water, as active ingredients, and wherein the active ingredients are present in an amount of 60 parts by weight;
b) at least one ingredient selected from the group consisting of:
oatmeal fiber,
psyllium seed gum,
chicory fiber,
Korean Solomon seal root powder,
green tea extract powder,
orange peel powder,
*Garcinia cambogia* extract powder, and
and alfalfa powder, wherein the at least one ingredient is present in an amount of 30 parts by weight; and
c) at least one ingredient selected from the group consisting of:
lecithin,
taurine,
L-carnitine,
vitamin C,
vitamin E,
vitamin A,
aspartame,
xylitol, and
oligosaccharides, wherein the at least one ingredient is present in an amount of 10 parts by weight.

6. An anti-obesity beverage comprising the anti-obesity composition as in any one of claims 2-5.

7. An anti-obesity frying powder comprising the composition of claim 1, in an amount of 20-40 parts by weight and starch powder in an amount of 60-80 parts by weight.

8. The anti-obesity frying powder of claim 7, wherein the frying powder is in a form selected from the group consisting of: a meat pad composition, wherein the meat pad composition is a hamburger, a sausage, or a hotdog.

9. An anti-obesity carbohydrate food composition comprising the anti-obesity frying powder of claim 8 and one or more carbohydrates selected from the group consisting of: rice powder, corn starch powder, potato starch powder, sweet potato starch powder, tapioca starch powder and wheat powder.

10. The anti-obesity carbohydrate food composition of claim 9 further comprising one or more ingredients selected from the group consisting of: sesame, jujube, carrot, old pumpkin, dried grape, Welsh onion, onions, garlic, red pepper, cabbage, Chinese cabbage, radish leaves, green tea leaves, eggplant, orange peels, celery, broccoli, cauliflower, tomato, chicory and spinach.

11. An anti-obesity beverage comprising the anti-obesity composition of claim 1.

12. An anti-obesity Kimchi comprising the anti-obesity composition of claim 1.

13. An anti-obesity powdered herbal tea composition comprising the anti-obesity composition of claim 1 and an herbal tea powder.

14. The anti-obesity powdered herbal tea composition of claim 13, which further comprises one or more extracts selected from the group consisting of: perfume of rosemary extracts, perfume of sage extracts, and perfume of rose extracts.

15. The anti-obesity powdered herbal tea composition of claim 14, which further comprises chicory powder.

16. An anti-obesity herbal tea beverage comprising the anti-obesity powdered herbal tea composition as in any one of claims 13-15.

17. An anti-obesity powdered green tea composition comprising the anti-obesity composition of claim 1 and a green tea powder.

18. An anti-obesity green tea beverage comprising the anti-obesity powdered green tea composition as in claim 17.

19. An anti-obesity soup powder comprising the anti-obesity composition of claim 1.

20. The anti-obesity vegetable soup powder of claim 19, further comprising Korean Solomon seal powder, endive leaf powder, starch powder, garlic powder, onion powder, ginger powder, red pepper or pepper powder, carrot powder, Chinese cabbage leaf powder, radish leaf powder, cabbage leaf powder, taurin, sesame powder and salt.

21. An anti-obesity vegetable sauce, a vegetable beverage, or a vegetable salad, comprising the anti-obesity composition of claim 1.

22. An anti-obesity milk product, comprising the anti-obesity composition of claim 1 in an amount of 1-10% by weight.

23. An anti-obesity alcoholic beverage, comprising the anti-obesity composition of claim 1 in an amount of 0.1-5% by weight.

* * * * *